(12) United States Patent
Salkowski et al.

(10) Patent No.: US 12,357,236 B2
(45) Date of Patent: Jul. 15, 2025

(54) BREAST BIOPSY IMMOBILIZATION DEVICE FOR MAGNETIC RESONANCE IMAGING

(71) Applicant: Wisconsin Alumni Research Foundation, Madison, WI (US)

(72) Inventors: Lonie Salkowski, Middleton, WI (US); Samuel Herzog, Kenosha, WI (US); Emma Brower, Savage, MN (US); Helen Treankler, Sobieski, WI (US); Gabrielle Ibrahim, Minneapolis, MN (US); Claire Swartz, Kenosha, WI (US); Cameron Ashford, Hudson, WI (US); Meghan Horan, Woodbury, MN (US); Kennedy Kruse, Village of Lakewood, IL (US); Eleanor Steger, Winnetka, IL (US)

(73) Assignee: Wisconsin Alumni Research Foundation, Madison, WI (US)

(*) Notice: Subject to any disclaimer, the term of this patent is extended or adjusted under 35 U.S.C. 154(b) by 405 days.

(21) Appl. No.: 18/081,925

(22) Filed: Dec. 15, 2022

(65) Prior Publication Data
US 2024/0197431 A1 Jun. 20, 2024

(51) Int. Cl.
*A61B 5/055* (2006.01)
*A61B 5/00* (2006.01)
*A61B 90/11* (2016.01)
*A61B 90/17* (2016.01)
*A61B 90/00* (2016.01)

(52) U.S. Cl.
CPC .............. *A61B 5/708* (2013.01); *A61B 5/055* (2013.01); *A61B 90/11* (2016.02); *A61B 90/17* (2016.02); *A61B 2090/374* (2016.02)

(58) Field of Classification Search
CPC ......... A61B 5/055; A61B 5/708; A61B 90/17; A61B 2090/374; A61B 8/403; A61B 6/0414
See application file for complete search history.

(56) References Cited

U.S. PATENT DOCUMENTS 5,050,197 A * 9/1991 Virta ...................... A61B 6/502
378/210
5,297,303 A * 3/1994 Stafford ............... A61B 6/0414
5/613

(Continued)

FOREIGN PATENT DOCUMENTS

CN 105228526 A * 1/2016 ............... A61B 6/03
CN 108652631 A * 10/2018 ......... A61B 10/0233

(Continued)

*Primary Examiner* — Colin T. Sakamoto
(74) *Attorney, Agent, or Firm* — Boyle Frederickson SC

(57) ABSTRACT

An MRI breast stabilization device optimizes the compression and immobilization of the breast during set-up before MRI imaging breast biopsy. The present invention provides breast support having a flat plate supporting a compression device that applies a uniform force against the breast tissue in an inward direction toward a biopsy grid plate (for legion localization). The breast tissue is held securely between the flat plate and the biopsy grid. The flat plate and the biopsy grid may support conventionally known breast coils that generate radiofrequency and/or receive magnetic signals from the MRI machine.

18 Claims, 4 Drawing Sheets

(56) References Cited

U.S. PATENT DOCUMENTS

| | | | | |
|---|---|---|---|---|
| 5,490,513 | A * | 2/1996 | Damadian | G01R 33/381 324/309 |
| 5,706,812 | A * | 1/1998 | Strenk | A61B 90/11 324/318 |
| 5,800,353 | A * | 9/1998 | McLaurin, Jr. | A61B 5/702 600/407 |
| 6,128,523 | A * | 10/2000 | Bechtold | A61B 5/055 601/4 |
| 6,778,848 | B1 * | 8/2004 | Bechtold | A61N 7/02 601/2 |
| 7,970,452 | B2 * | 6/2011 | Piron | A61B 90/14 5/601 |
| 2001/0039378 | A1 * | 11/2001 | Lampman | A61B 90/10 600/410 |
| 2002/0156365 | A1 * | 10/2002 | Tsekos | A61B 5/708 600/417 |
| 2005/0080333 | A1 * | 4/2005 | Piron | G01S 7/52049 600/417 |
| 2005/0207528 | A1 * | 9/2005 | Hjarn | A61B 6/0414 378/37 |
| 2007/0135821 | A1 * | 6/2007 | Shabaz | A61B 10/02 600/564 |
| 2008/0071164 | A1 * | 3/2008 | Pogue | A61B 5/055 600/411 |
| 2008/0077005 | A1 * | 3/2008 | Piron | A61B 5/055 600/411 |
| 2009/0012388 | A1 * | 1/2009 | Harter | A61B 5/055 600/422 |
| 2009/0171244 | A1 * | 7/2009 | Ning | A61B 6/0435 378/37 |
| 2010/0283466 | A1 * | 11/2010 | Krieg | A61B 5/708 324/318 |
| 2010/0331699 | A1 * | 12/2010 | Yu | A61B 8/0825 600/446 |
| 2013/0116570 | A1 * | 5/2013 | Carson | A61B 6/502 600/459 |
| 2014/0121499 | A1 * | 5/2014 | Coppens | A61B 5/704 600/422 |
| 2014/0128723 | A1 * | 5/2014 | Yang | A61B 10/0233 600/417 |
| 2014/0213886 | A1 * | 7/2014 | Menon | A61B 5/708 600/411 |
| 2015/0168509 | A1 * | 6/2015 | Yang | A61B 90/17 600/567 |
| 2016/0033589 | A1 * | 2/2016 | Ota | G01R 33/3415 600/417 |
| 2017/0238884 | A1 * | 8/2017 | Jeong | A61B 5/0051 |
| 2018/0280108 | A1 * | 10/2018 | Kevin | A61B 90/17 |
| 2020/0060633 | A1 * | 2/2020 | Radicke | A61B 6/4417 |
| 2020/0093440 | A1 * | 3/2020 | Small | A61B 6/0414 |
| 2020/0367855 | A1 * | 11/2020 | Park | A61B 8/406 |
| 2021/0015435 | A1 * | 1/2021 | Defreitas | A61B 6/502 |
| 2021/0022705 | A1 * | 1/2021 | Suzuki | A61B 8/15 |
| 2024/0115223 | A1 * | 4/2024 | Gennari | A61B 6/502 |
| 2024/0180509 | A1 * | 6/2024 | Defreitas | A61B 6/502 |

FOREIGN PATENT DOCUMENTS

| | | | | |
|---|---|---|---|---|
| DE | 19610802 | A1 * | 9/1997 | ........ A61B 6/0414 |
| DE | 19707451 | A1 * | 8/1998 | ........ A61B 5/055 |
| DE | 19834585 | A1 * | 2/2000 | ........ A61B 5/0555 |
| DE | 202019104887 | U1 * | 11/2019 | |
| WO | WO-0016695 | A1 * | 3/2000 | ........ A61B 6/0414 |
| WO | WO-2022048979 | A1 * | 3/2022 | |

* cited by examiner

BREAST BIOPSY IMMOBILIZATION DEVICE FOR MAGNETIC RESONANCE IMAGING

STATEMENT REGARDING FEDERALLY SPONSORED RESEARCH OR DEVELOPMENT

--

CROSS-REFERENCE TO RELATED APPLICATIONS

--

BACKGROUND OF THE INVENTION

About 1 in 8 women in the United States will develop invasive breast cancer during their lifetime and approximately 290,000 new cases of breast cancer are diagnosed each year. In the U.S., breast cancer is currently the most common cancer diagnosed. Early detection of breast cancer can increase the treatment options and survival rate for patients.

Magnetic resonance imaging (MRI) provides more sensitive breast imaging (~90% detection rate) compared to mammography or ultrasound, and therefore, is an adjuvant imaging modality for high risk patients. Breast MRI can be used for both diagnostic imaging and MRI-guided biopsy where MRI assists with localizing lesions for image guided biopsy.

During MRI of the breast, the patient lies in a prone position on a scanning table. Good imaging relies on stabilization of breast tissue which has its own unique challenges because of the highly deformable nature of breast tissue, the extension of breast tissue perpendicular to the stable longitudinal axis of the body, and variations in breast shape and size between patients (e.g., ranging from bra cup size A to DD).

Conventionally, the breast support used for MRI biopsies utilizes two-dimensional parallel plates (one with a gridded structure and one flat plate) to compress the breast tissue into a flat shape and immobilize the breast tissue during the interventional procedure. It is desirable to position the breast between the parallel plates in a manner which maximizes the area of visible breast tissue, minimize skin folding, and achieves uniform compression. However, thinner areas of the breast are often not well compressed, for example, the nipple-areolar complex and the outer margins (peripheral areas) of the breast, leading to poor visualization and access.

It is therefore commonplace for medical professionals to improvise by using foam wedges, sponges, or small saline bags to compress the breast tissue at these peripheral areas. The set-up time to prepare the patient for MRI scanning is therefore increased leading to interventional procedure inefficiencies and increased discomfort to the patient. Furthermore, there is increased risk of incomplete, cancelled, or poor quality MRI scans.

Therefore, it is difficult to provide stability to the breast tissue and uniformity in patient care using conventional medical equipment.

SUMMARY OF THE INVENTION

The present invention provides an MRI breast stabilization device which optimizes the compression and immobilization of the breast during set-up before breast MRI biopsy. The present invention provides a breast support having a flat plate supporting a novel compression device that applies a uniform force against the breast tissue in an inward direction toward an opposed biopsy grid plate (for legion localization). Therefore, breast tissue is held securely between the flat plate and the biopsy grid. The flat plate and the biopsy grid may support conventionally known breast coils that generate radiofrequency and/or receive magnetic signals from the MRI machine.

Generally, a padded scanning table supporting the breast support may include bores receiving downwardly extending breasts therein and which allow the breast support of the present invention to compress the downwardly extending breasts. The breast support may assist with positioning a plurality of local radiofrequency (RF) coils adjacent to the breasts while the breasts are in the bores of the table. In a typical arrangement, several adjacent coils are provided for receiving nuclear magnetic resonance (NMR) signals which are given off by protons in the body in the presence of a strong magnetic field after excitation by RF signals during MR imaging. The scanning table is slid into the opening of the MRI machine to begin scanning as conventionally known in the art.

In one embodiment of the present invention, the compression device of the breast support is a hinged plate that pivots inward in an upward direction (toward the breast) to compress the breast tissue inward and upward toward the laterally or medially positioned biopsy grid. The hinged plate is swung inward to apply a force on the breast by the force of an expandable insert that increases in volume as it expands, thus moving the hinged plate toward the breast tissue and pressing the hinged plate against the breast tissue to create a tight compression of breast tissue against the biopsy grid.

In an alternative embodiment of the present invention, the compression device of the breast support is an inflatable bladder that is filled with a fluid, e.g., a gas such as air or liquid such as normal saline, and the like, to increase the volume of the bladder to compress the breast tissue toward the laterally or medially positioned biopsy grid to create a tight compression of breast tissue against the biopsy grid. The inflatable bladder has a generally J-shaped cross section (taken perpendicular to compression) to cradle the nipple-areola complex or anterior region of the breast without contacting the nipple, and to support the breast in an upward direction by providing multiple degrees of freedom during compression.

It is thus a feature of at least one embodiment of the present invention to provide complete and sustained purchase of the breast against the biopsy grid plate, in particular, for smaller sized breasts, and to prevent "skiving" or uncontrolled tissue or lesion movement during MRI assisted biopsy.

It is also a feature of at least one embodiment of the present invention to assist with visibility of lesions in difficult to image areas, such as too thinly compressed tissue at the breast margins, tissue close to the skin surface, and tissue of the nipple-areolar complex.

Specifically, one embodiment of the present invention provides a breast immobilization device for magnetic resonance imaging (MRI) assisted biopsy of a breast having a medial or lateral side of the breast extending along a biopsy grid extending along a plane and an opposite side of the breast extending along a flat plate extending parallel to the plane. The device comprises an expandable volume positioned between the biopsy grid and the flat plate, in a first unexpanded position, having a first thickness measured perpendicular to the plane, and in a second expanded position, having a second thickness measured perpendicular to the plane that is greater than the first thickness. The volume in the second expanded position exerts a force against the opposite side of the breast to press the medial or lateral side of the breast against the biopsy grid.

The expandable volume may be an inflatable bladder comprising a silicone housing.

It is thus a feature of at least one embodiment of the present invention to provide a uniform compression of the breast in multiple dimensions to minimize anatomic distortion of the breast tissue.

The inflatable bladder may provide a planar attachment surface opposite a concave contact surface contacting an anterior margin of the patient's breast. The inflatable bladder may provide a J-shaped cross section taken perpendicular to the plane.

It is thus a feature of at least one embodiment of the present invention to provide inward and upward compression on the breast while the patient is laying prone to "cradle" the anterior breast without the bladder contacting the nipple.

The bladder may be fillable with a fluid. The fluid may be at least one of air or saline.

It is thus a feature of at least one embodiment of the present invention to utilize MRI compatible fluids which mimic breast tissue properties (e.g., density) to provide deformable compression of the breast without introducing imaging interference.

A pump may be configured to fill the bladder with the fluid. The pump may be a manual balloon pump. Alternatively, the pump may provide an automated delivery of pressurized air, such as by an electric air compressor.

It is thus a feature of at least one embodiment of the present invention to provide real-time manual or electric control of the amount of compression placed on the patient breast. Compression may occur in an open or closed loop system where the closed system will include at least one sensor communicating with the pump.

The volume may be a memory foam.

It is thus a feature of at least one embodiment of the present invention to use the natural "visco-elasticity" of memory foam to provide comfortable slow compression of the breast tissue using the natural tendency of memory foam to expand to its original shape.

The volume may further comprise a plate pivotable with respect to the expandable volume to pivot toward the opposite side of the breast when the expandable volume goes from the first unexpanded position to the second expanded position.

It is thus a feature of at least one embodiment of the present invention to minimize patient discomfort and decrease patient set up time.

The expandable volume may be positioned between the pivotable plate and the flat plate.

It is thus a feature of at least one embodiment of the present invention to provide medial/lateral compression while leaving access for opposite lateral/medial breast approach for needle insertion during a needle breast biopsy.

The device may further comprise the biopsy grid and flat plate wherein the expandable volume is attached to the flat plate.

It is thus a feature of all embodiments of the present invention to permit the placement of any commercially available RF coils about the breast and to not deleteriously affect the transmission of RF waves through the breast tissue.

A difference between the first thickness and the second thickness may be at least 1.5 inches. A difference between the first thickness and the second thickness may be at least 3 inches.

It is thus a feature of at least one embodiment of the present invention to provide sufficient breast compression to allow the reference point position to be viewed through the biopsy grid and to allow for needle insertion without substantial movement of breast tissue.

An alternative embodiment of the present invention provides a method of breast immobilization for magnetic resonance imaging (MRI) assisted biopsy of a patient breast, the method comprising extending a medial or lateral side of the patient breast along a biopsy grid extending along a plane and an opposite side of the breast along a flat plate extending parallel to the plane; positioning an expandable volume between the biopsy grid and the flat plate, wherein in a first unexpanded position, the volume has a first thickness measured perpendicular to the plane, and in a second expanded position, the volume has a second thickness measured perpendicular to the plane that is greater than the first thickness; and exerting a force against the opposite side of the breast to press the medial or lateral side of the breast against the biopsy grid in the second expanded position of the volume.

The expandable volume is an inflatable bladder and the method further comprises filling the inflatable bladder with a fluid.

The expandable volume is a memory foam and the method further comprises deforming the memory foam and allowing the memory foam to return to its original state.

These particular objects and advantages may apply to only some embodiments falling within the claims and thus do not define the scope of the invention.

DETAILED DESCRIPTION OF THE INVENTION

Figure 1:
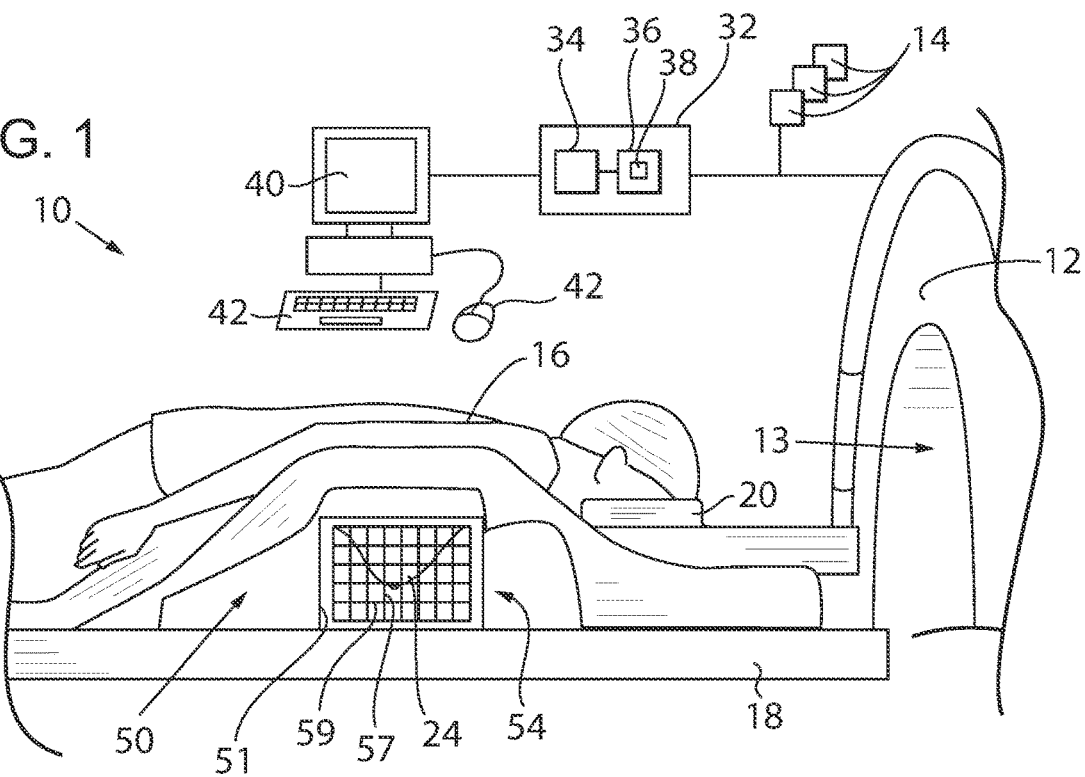
FIG. 1 is a side perspective view of a breast immobilization device of the present invention for breast MRI for use with a breast coil assembly including a padded scanning table, coil elements, an immobilization plate supporting a compression device, and a biopsy grid.
Figure 2:
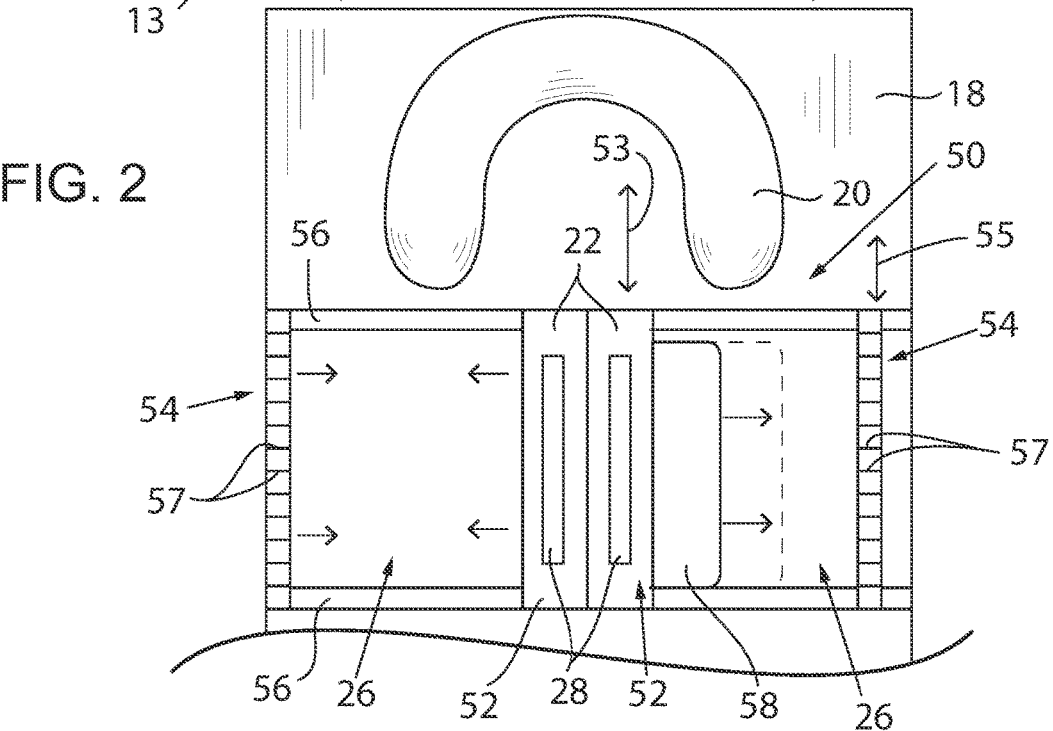
FIG. 2 is a schematic top plan view of the breast immobilization device of FIG. 1.

FIGS. 1 and 2 is an assembly 10 for breast magnetic resonance imaging (MRI) of the present invention for use with an imaging scanner such as an MRI scanner 12 or the like. The assembly 10 may provide for high resolution image scans 14 presenting anatomical information about a patient 16. The MRI scanner 12 has a large central opening or bore 13 receiving a padded scanning table 18 therethrough supporting the laying patient 16 in a prone position.

The padded scanning table 18 is slid into an opening or bore 13 of the MRI scanner 12 head first (as shown) or feet first. The padded scanning table may include specific padding to support the patient's head and sternum such as a head rest 20 and a medial sternum cushion 22 which allow a patient's breasts 24 to comfortably extend downwardly into depressions or bores 26 within the padded scanning table 18. The bores 26 are sized to receive a range of breast sizes with an average breast size being approximately 6 inches in diameter and 4 inches in height (while the patient is lying in prone position).

The MRI scanner 12 creates a magnetic field around the patient 16 and radio waves are directed into the patient's body. Imaging of the patient's breasts 24 is facilitated by dedicated breast coils 28 surrounding the breasts 24 that detect magnetic signals from the MRI scanner 12. The bores 26 may support dedicated breast coils 28 that generate radiofrequency and/or receive magnetic signals from the MRI scanner 12 and which may be provided by plates flanking the breasts as will be described in greater detail below.

In general, the MRI scanner 12 will provide high-resolution image scans 14 from the imaging MRI scanner 12. In each case, the image scans 14 will present dimensions of information associated with volume elements (voxels) distributed in three dimensions within a volumetric region of interest (i.e., breast tissue) in the patient 16. A contrast agent, such as contrast dye like Gadolinium, may be injected into an intravenous line in the patient 16 to differentiate possibly malignant lesions within the breast tissue by making their MR signal relatively higher than the normal background tissue in the image scans 14 easier to see.

These scans 14 will be repeated at different times throughout the course of obtaining biopsies of the patient 16, for example, before or after breast biopsy. Scans may be performed before or after other forms of medical imaging such as a mammogram to provide more sensitivity when screening for potentially malignant lesions or characterizing questionable regions of the breast detected by other modalities.

Referring specifically to FIG. 1, the MR raw data is received by a coil which is then digitizes and transformed into image scans 14 by an electronic computer 32 for processing. Generally, the electronic computer 32 includes one or more processing units 34 communicating with a memory 36 holding data and a stored program 38 for effecting portions of the present invention. The computer 32 may communicate with a graphics display 40 for displaying output images based on the image scans 14 and may further communicate with user input devices 42 such as a keyboard, mouse or the like, each allowing entry of data by a user. The invention will provide an output on the display 40 indicating breast health such as cancer or lesion detection, cancer or lesion localization, cancer or lesion progression or regression, or the like based on image scans of the patient's breast 24.

Referring specifically now to FIG. 2, the assembly 10 for breast magnetic resonance imaging (MRI) further includes a breast stabilization device 50 that creates a space for the pendant breast of the prone patient to reside during imaging. The patient's sternum and shoulders and lateral regions of their torso rest on the padded supports of the scanning table 18 allowing the breast stabilization in order to compress and immobilize the breasts 24 during scanning. The breast stabilization device 50 may also support the dedicated radio frequency (RF) coils or breast coils 28 and their electrical connectors for breast MRI. For example, the breast coils 28 may be loop coils located centrally on each breast or laterally on the sides of the breasts.

The breast stabilization device 50 may provide for an immobilization plate 52 extending along a first plane 53 positioned along a first, medial/lateral side of the breast 24, and a biopsy grid 54 extending along a second plane 55 positioned along a second, opposite lateral/medial side of the breast 24 such that the immobilization plate 52 and biopsy grid 54 are parallel plates flanking the breast 24. The immobilization plate 52 will support a compression device 58 that expands after the breast 24 is positioned between the immobilization plate 52 and biopsy grid 54 to compress the breast against the biopsy grid 54 as will be described in greater detail below.

The immobilization plate 52 may be a rigid rectangular plate that extends downwardly along one side of each of the bores 26 and sized to be at least as large as the dimensions of the breast 24 (while the patient is lying in prone position). The size of the immobilization plate 52 may be 4 to 6 inches and approximately 5 inches in height, by 8 to 10 inches and approximately 9 inches in width.

The biopsy grid 54 extends downwardly along an opposite side as the immobilization plate 52 of each of the bores 26. The biopsy grid 54 may be a rigid rectangular frame 51 supporting a pattern of horizontal rails 59 and vertical rails 57 defining square openings which permit the user to mark and localize a lesion within the breast 24 and permit needle biopsy access to the breast 24. The biopsy grid 54 may support a needle block (not shown) which permits unidirectional insertion of the biopsy needle into the breast 24. In one embodiment, the biopsy grid 54 is 3 to 7 inches and approximately 5 inches in height, by 5.5 to 9.5 inches and approximately 7.5 inches in width, by 0.3 to 0.7 inch and approximately 0.5 inch in depth, with square openings, for example, 24 units, that are 0.5 to 1 inch by 0.5 to 1 inch and approximately 0.7 inch by 0.7 inch.

At least one of the immobilization plate 52 and the biopsy grid 54 may support the dedicated breast coils 28 comprising coil elements used with assisting with the detection of magnetic signals from the MRI scanner 12. For example, a breast coil 28 may be formed within the immobilization plate 52 (as shown) and/or may surround or frame the biopsy grid 54 for example, a rectangular-shaped loop coil surrounding the rectangular biopsy grid. A dedicated breast coil 28 may be positioned on the lateral and/or medial side of the non-imaged breast as well. The breast coils 28 may be interchangeable to allow for various elements of the breast stabilization device 50 such as the immobilization plate 52 and the biopsy grid 54 to be re-positioned, for example, switched medially or laterally, to suit different patients and biopsy procedures.

The breast coils 28 may be breast coils that are commercially available from a variety of sources including Invivo Corporation's Sentinelle Breast Coil system described in U.S. Pat. Nos. 8,744,550 and 9,770,209, hereby incorporated by reference.

As understood, the breast coils 28 may receive and convert the magnetic signal into data that get transferred into electronic computer 32 and processed to form the final image on the graphics display 40. The quality of the MRI images depends on the signal-to-noise ratio (SNR) of the acquired signal from the patient 16.

The immobilization plate 52 and/or the biopsy grid 54 may be supported on a transverse slider track or tracks 56 perpendicular to the plates 53, 55 to allow the immobilization plate 52 and/or the biopsy grid 54 to be moved along the track 56 closer or further away from the other plate. The immobilization plate 52 and/or the biopsy grid 54 are slid along the track 56 for initial positioning and stabilization of the breast 24 between the parallel plates 52, 54, however, a more finely-tuned enhanced compression may be accomplished by the compression device 58 which is supported by the immobilization plate 52 and which may be expanded after the breast 24 is positioned between the immobilization plate 52 and biopsy grid 54 as will be described in greater detail below.

The compression device 58 may take multiple forms with exemplary embodiments described below.

First Embodiment

Figure 3:
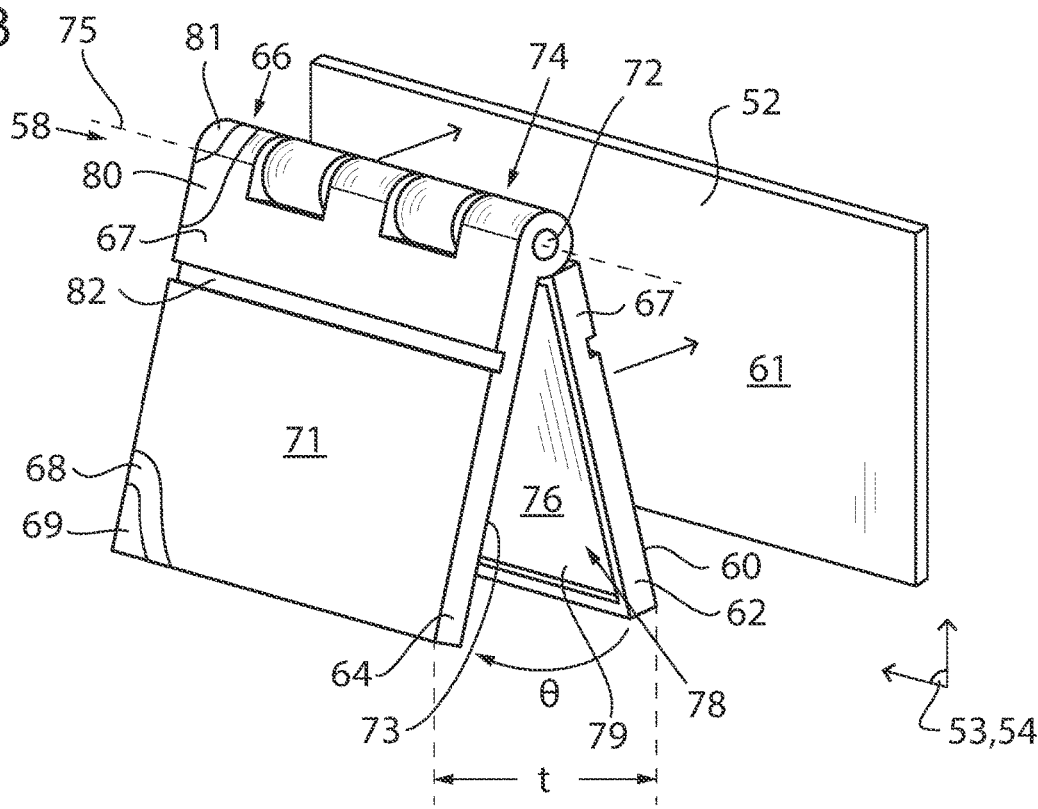
FIG. 3 is a perspective view of the compression device of a first embodiment of the present invention having a pivotable plate and a stationary plate attachable to the immobilization plate.
Figure 4:
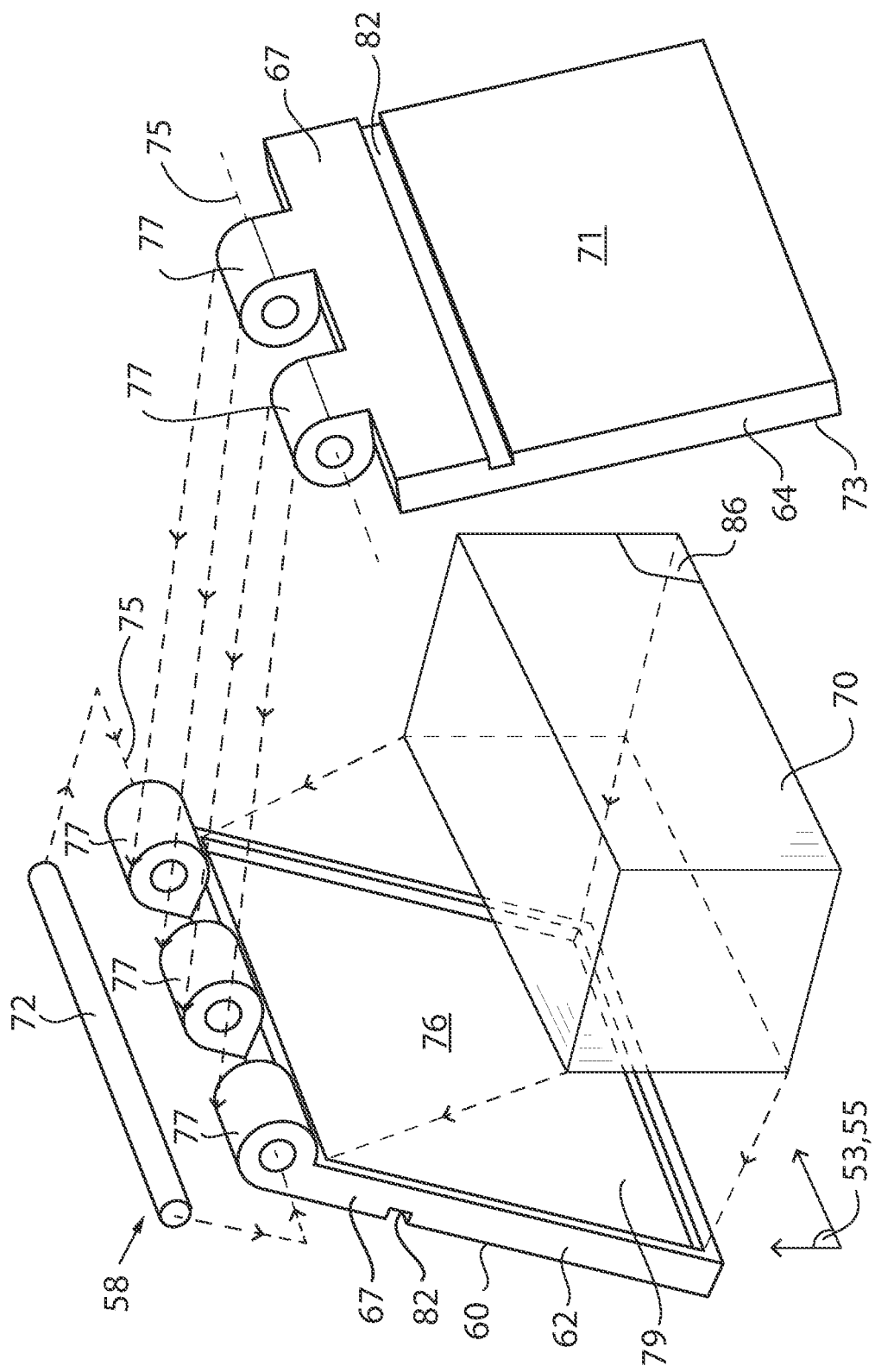
FIG. 4 is an exploded view of the compression device of FIG. 3 showing an expandable insert attachable between the pivotable plate and the stationary plate.

Referring to FIGS. 3 and 4, in one embodiment of the present invention, the compression device 58 attached to the immobilization plate 52 is a jointed or hinged device having a stationary leaf 62 hinge-connected to a movable leaf 64 along a joint 66 at upper edges 67 of the stationary leaf 62 and movable leaf 64, respectively, to provide pivotable movement of the movable leaf 64 toward and away from the lateral/medial breast 24. The stationary leaf 62 is fixedly attached to the immobilization plate 52 of the breast stabilization device 50 while the movable leaf 64 is positioned to pivot away from the stationary leaf 62 and immobilization plate 52 to contact the patient's breast 24.

The stationary leaf 62 may be a rigid rectangular plate. The stationary leaf 62 may be attached to the immobilization plate 52 to extend along the first plane 53 by an adhesive such as glue, tape, hook and loop fasteners such as Velcro or straps secured using an adhesive or fasteners, which allow the back surface 60 of the stationary leaf 62 to be adhered to a front surface 61 of the immobilization plate 52. The stationary leaf 62 may have dimensions of 4 to 6 inches and approximately 5 inches in height, by 8 to 10 inches and approximately 9 inches in width, which may be generally similar to or smaller than the dimensions of the immobilization plate 52.

The movable leaf 64 may be a rigid rectangular plate and may be similar or identical to the construction of the stationary leaf 62. The movable leaf 64 may be connected by a hinge to the stationary leaf 62 at the upper edge 67. A front surface 71 of the movable leaf 64 is directed away from the stationary leaf 62 to contact the patient's breast 24 while a rear surface 73 of the movable leaf 64 faces toward the stationary leaf 62. The movable leaf 64 may have dimensions of 4 to 6 inches and approximately 5 inches in height, by 8 to 10 inches and approximately 9 inches in width. The size of the movable leaf 64 may be approximately the same size as the stationary leaf 62 and may be at least as large as the size of an average breast.

The front surface 71 of the movable leaf 64 which contacts the patient's breast 24 may support a layer of padding 68, for example, memory foam, to provide additional comfort to the patient 16. The padding 68 may further include a protective cover 69 such as a biocompatible material of medical grade nylon or the like which may safely contact the patient's skin. The protective cover 69 may also be a stretchable and soft material.

The joint 66 joining the stationary leaf 62 and the movable leaf 64 and allowing for free rotation of the stationary leaf 62 with respect to the movable leaf 64 may be a hinge defined by a pin or dowel 72, or the like, inserted into a barrel 74 of the hinge and extending along an axis 75 of the upper edges 67 of the stationary leaf 62 and movable leaf 64, respectively. In one embodiment, the barrel 74 may comprise of multiple cylinders 77 of the stationary leaf 62 (e.g., two or three cylinders) and movable leaf 64 (e.g., two or three cylinders), respectively, which alternate between the stationary leaf 62 and movable leaf 64 and interlock to receive the dowel 72 through openings of the cylinders 77 extending along the axis 75. The barrel 74 may be 0.5 to 2 inches and approximately 1 inch in height, and 8 to 9 inches and approximately 8.5 inches in width (with each cylinder approximately 2 inches in width with approximately 1 inch gaps between cylinders). The dowel 72 may have a length of 8 to 9 inches and approximately 8.5 inches and may have a 0.25 to 1 inch and approximately ⅜ inch diameter.

A rectangular shaped hinge padding 80 may further extend over and cover the upper exposed end of the barrel 74 to provide patient comfort when the patient's sternum rests upon the barrel 74, for example, when the immobilization plate 52 extends along the medial breast 24. The hinge padding 80 may further include a protective cover 81 such as a biocompatible material of medical grade nylon or the like which may safely contact the patient's skin and may be a stretchable and soft material.

Grooves 82 extending in and across an upper end of the front surface 71 of the movable leaf 64 and an upper end of the rear surface 60 of the stationary leaf 62 may assist with the attachment of the hinge padding 80, for example, permitting attachment straps along the lower edges of the hinge padding 80 to extend along and within the grooves 82 and attached or fastened around the stationary leaf 62 and movable leaf 64. The grooves 82 may be 0.1 to 0.2 inch and approximately 0.15 inch deep, by 0.2 to 0.3 inch and approximately 0.25 inch in height, by 8 to 10 inches and approximately 9 inches in width.

The stationary leaf 62 and the movable leaf 64 may be manufactured of a thermoplastic polyester such as polylactic acid (PLA) or the like and may be made of a material that is capable of three dimensional (3D) printing. The dowel 72 may be manufactured of a wood material, plastic material, or the like. Other materials suitable for the parts of the breast stabilization device 50 include glass, nylon, Teflon, and various plastics, or the like which are MRI compatible and do not contain magnetic or ferrous metal which would interfere with the MRI.

An interior space 78 situated between the stationary leaf 62 and the movable leaf 64 is configured to support an expandable insert 70 which is expandable to increase in size and volume. The expandable insert 70 may be attached to an inner surface 73, 76 of at least one of the stationary leaf 62 and movable leaf 64, for example, by adhesive or hook and loop fasteners such as Velcro. The adhesive or fasteners may allow the expandable insert 70 to be easily removed and replaced, for example, to change the desired size of the insert 70.

A rectangular depression 79 within the inner surface 73, 76 of the stationary leaf 62 and movable leaf 64 may assist with the attachment of the expandable insert 70, for example, receiving the adhesive or fasteners attaching the expandable insert 70 therein. The rectangular depression 79 may be 0.1 to 0.2 inch and approximately 0.15 inch deep by 3 to 5 inches and approximately 4 inches in height by 7 to 9 inches and approximately 8 inches in width and may be approximately the same height and width as the height and width of the expandable insert 70.

In one embodiment, the expandable insert 70 is a memory foam, or a "viscoelastic" polyurethane foam or low-resistance polyurethane foam (LRPu), or the like. The expandable insert 70 is elastic and viscous to change back to its original shape (expanded shape) slowly over time after deformation. The expandable insert 70 may expand evenly in all directions or may preferably expand perpendicular to the parallel planes 53, 55 and perpendicular to the inner front surface 76 of the stationary leaf 62 (or inner rear surface 73 of the movable leaf 64) to which it is attached. The expandable insert 70 is dense enough to provide a sufficient force against the breast 24 to deform the breast 24.

The expandable insert 70 may be a rectangular block, for example, of memory foam material, with the block varying in size (in an expanded state) to provide various depths and angulation of the movable leaf 64 with respect to the stationary leaf 62. The expandable insert 70 may be a rectangular block and may vary in size, for example, 1.5 to 3 inches depth by 3 inches height by 8 inches width. For example, a small block may be 1.5 inches depth by 3 inches height by 8 inches width and a large block may be 3 inches depth by 3 inches height by 8 inches width.

As the expandable insert 70 expands in size and volume, it will swing or pivot the movable leaf 64 away from the stationary leaf 62 at varying angles. The angulation (θ) of the movable leaf 64 with respect to the stationary leaf 62 may vary between 10 to 60 degrees and approximately 30 degrees. An overall thickness (t) of the compression device 58, measured perpendicular to parallel planes 53, 55 and defined by the greatest depth of the stationary leaf 62 to the movable leaf 64, increases as the movable leaf 64 pivots away from the stationary leaf 62. The overall thickness (t) of the compression device 58 may increase at least 1.5 inches and at least 3 inches through the expansion of the expandable insert 70.

It is understood that the expandable insert 70 may take various shapes and forms such as wedge shaped or circular shaped memory foam blocks that are inserted into the interior space 78 between the stationary leaf 62 and the movable leaf 64 and which increase in depth when expanded. It is also understood that the expandable insert 70 may be fillable bladders or other expandable materials or constructions such as springs which allow the movable leaf 64 to pivot and the overall thickness (t) to increase.

The expandable insert 70 may be wrapped in a protective cover 86 such as a biocompatible material of medical grade nylon or the like. The protective cover 86 may be a stretchable and soft material.

In use, the expandable insert 70 is attached to an inner surface 73, 76 of the stationary leaf 62 or movable leaf 64 and deformably compressed, for example, by manually pressing the movable leaf 64 toward the stationary leaf 62 prior to the insertion of the patient's breast 24 between the immobilization plate 52 and the biopsy grid 54.

After the patient's breast 24 is inserted between the immobilization plate 52 and the biopsy grid 54, the movable leaf 64 is released and the expandable insert 70 is allowed to slowly expand to recover its original shape and further pivot the movable leaf 64 toward the breast 24 to press upward and inward laterally/medially against the breast compressing the breast 24 against the biopsy grid 54.

As shown in FIGS. 1 and 2, the biopsy grid 54 is positioned adjacent the lateral side of the breast and the movable leaf 64 pivots forward against the medial side of the breast to compress the breast 24 against the biopsy grid 54. It is understood that the biopsy grid 54 may alternatively be positioned adjacent the medial side of the breast 24 and the movable leaf 64 pivots rearward against the lateral side of the breast 24 to compress the breast 24 against the biopsy grid 54. Following expansion of the expandable insert 70, the breast 24 may be manually maneuvered and repositioned to provide even compression of the breast tissue against the biopsy grid 54.

The expandable insert 70 may be removed and replaced with a differently sized expandable insert 70 if greater or lesser compression of the breast 24 is desired. The compression device 58 may include a kit or set of expandable inserts 70 of different sizes (e.g., small, medium, large) that can be interchanged.

The joint 66 of the compression device 58 permits free rotation in one direction (e.g., angled inward and upward) of the movable leaf 64 against the breast 24. The force of the movable leaf 64 applied against the breast 24 is provided in two dimensions, like parallel plates 52, 54, but is an improvement over parallel plates by providing an upward angle of compression, in addition to inward compression, which provides improved compression of the outer areas or margins of the breast 24. Desirably, all areas of the breast tissue are fully flush against the biopsy grid 54, where flush is when the grid square of the biopsy grid 54 is filled with tissue and the tension of the tissue allows for insertion of a biopsy needle without tissue movement.

Second Embodiment

Figure 5:
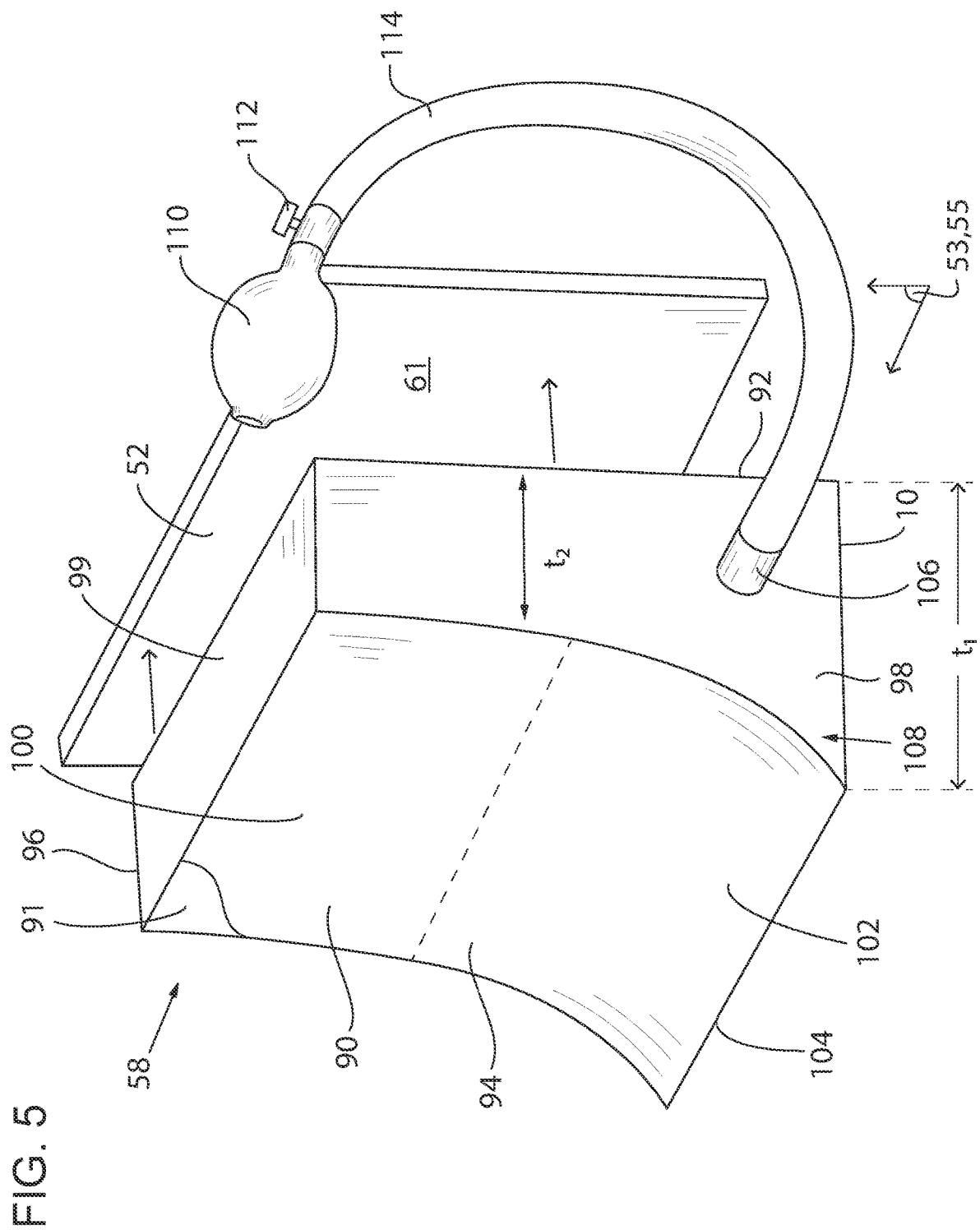
FIG. 5 is a perspective view of the compression device of a second embodiment of the present invention having an inflatable bladder attachable to the immobilization plate.

Referring to FIG. 5, in an alternative embodiment, the compression device 58 of the immobilization plate 52 is an inflatable device defined by a balloon or bladder 90 attached to the immobilization plate 52 and expandable by a fluid, e.g., gas such as air or liquid such as normal saline, to increase an overall thickness (t) of the compression device 58 measured perpendicular to the parallel planes 53, 55 and the front surface 61 of the immobilization plate 52 to which it is attached.

The bladder 90 comprises a ramp shaped housing that is fillable with a fluid to expand in size and volume. The bladder 90 housing may comprise a rear wall 92 attachable to the immobilization plate 52 opposite a curved front wall 94 contacting the patient's breast 24 and flanked by left and right sidewalls 96, 98. The left and right sidewalls 96, 98 may be generally J-shaped walls. Top and bottom rectangular walls 99, 101 enclose the top and bottom edges of the rear and front walls 92, 94 and left and right sidewalls 96, 98. The housing of the bladder 90 may be air-tight sealed to prevent leakage of the fluid.

The curved front wall 94 may be 8 to 9 inches and approximately 8.75 inches in width and 5 to 6 inches and approximately 5.5 inches in height. The curved front wall 94 has a top portion 100 (approximate top half) that extends parallel to the planar rear wall 92 and a lower portion 102 (approximate bottom half) that curves outward from the top portion 100 to a bottom edge 104 to provide a concave lower portion 102 resembling a ramp. The curvature of the lower portion 102 may have an arc length of approximately 6 inches, a chord length of approximately 5.8 inches, and a diameter of approximately 15 inches, which generally aligns with the curvature of the anterior breast 24 (while the patient is lying in a prone position). The curved front wall 94 generally expands to contact and apply pressure to the patient's breast 24.

The rear wall 92 may be 5 to 6 inches and approximately 5.5 inches in height and 8 to 9 inches and approximately 8.75 inches in width. The left and right sidewalls 96, 98 may be 1.5 to 3 inches and approximately 2 inches depth at the top portion 100 and approximately 2 to 4 inches depth at the lower portion 102 and 4 to 6 inches and approximately 5 inches in height. The top rectangular wall 99 may be 1.5 to 3 inches and approximately 2 inches depth and 8 to 9 inches and approximately 8.7 inches in width. The bottom rectangular wall 101 may be 3 to 4 inches and approximately 3.85 inches depth and 8 to 9 inches and approximately 8.7 inches in width.

The rear wall 92 bladder 90 may be attached to the immobilization plate 52 by an adhesive such as glue such as silicone caulk, tape, hook and loop fasteners such as Velcro or straps secured using an adhesive or fasteners, which allow the rear wall 92 of the bladder 90 to be adhered to a front surface 61 of the immobilization plate 52.

A tube connector 106, such as a connector with a Luer lock fitting or similar system, may be attached to the bladder 90 and may fluidly communicate with an interior volume 108 of the bladder 90 to allow for the interior volume 108 to be filled with the fluid from an external fluid source. The tube connector 106 may be positioned on either or both sidewalls 96, 98 of the bladder 90 to allow the bladder 90 to be easily adapted for use on either side (lateral/medial breast) of the breast or either breast (left or right) of the patient. It is also understood that the tube connector 106 may be positioned on any other wall of the bladder 90 housing in a similar manner.

The external fluid source may be a pump 110 having a one way valve 112 which permits one way fluid flow from the pump 110 through a medical grade tubing 114 and through the tube connector 106 of the bladder 90. In one embodiment, the pump 110 is a manual pump which may be a balloon pump (as shown) that is manually repeatedly squeezed to push air from the balloon through the medical tubing 114 and into the bladder 90. In an alternative embodiment, the pump 110 is an electrically powered pump (shielded or positioned outside of the shielded MRI room) which may be a motor or air compressor with an electric valve system which controls air flow and pushes air from the compressor through the medical tubing 114 and into the bladder 90 and may be desired for moving the air through longer medical tubing 114. The electrically powered pump may be operated by the user by a switch.

The bladder 90 and the tube connector 106 may be manufactured of an elastomer (elastic polymer) or rubber-like polymer, or non-ferrous, non-metallic or non-paramagnetic polymer, such as silicone, for example, commercially available Dragon Skin™ silicone sold by Smooth-On or the like and may be capable of being molded with 3D printed positive and negative molds made of a thermoplastic polyester such as polylactic acid (PLA) or polyvinyl alcohol (PVA). The bladder 90 may be manufactured of one or more separate parts that are joined to form the housing.

The bladder 90 may be further wrapped in a protective cover 91 such as a biocompatible material of medical grade nylon or the like. The protective cover 91 may be a stretchable and soft material.

The desired wall thickness of the bladder 90 wall may be 0.2 to 0.3 inch and approximately 0.25 inch. The bladder 90 may expand evenly in all directions and may preferably expand in depth or overall thickness (t), measured perpendicular to parallel planes 53, 55 and the front surface 61 of the immobilization plate 52 to which it is attached. The bladder 90 may expand at least 1.5 inches and at least 3 inches in overall thickness (t). The thickness ($t_1$) of the lower portion 102 is generally greater than the thickness ($t_2$) of the upper portion 100. A difference between thickness ($t_1$) and thickness ($t_2$) may be 0.5 inch to 3 inches.

It is also understood that the bladder 90 may be replaced by other expandable materials or constructions such as memory foam which expand to directly contact the patient's breast 24 and causes the overall thickness (t) to increase.

In use, the bladder 90 in a deflated or partially inflated state is attached to the immobilization plate 52 prior to the insertion of the patient's breast 24 between the immobilization plate 52 and the biopsy grid 54. The bladder 90 may be partially inflated to allow for a cushion for patient comfort.

After the patient's breast 24 is inserted between the immobilization plate 52 and the biopsy grid 54, the bladder 90 is more fully inflated by the pump 110 and the fluid is inserted into the bladder 90 to enlarge the bladder 90 to press the curved front wall 94 of the bladder 90 against the breast 24, and to press inward, compressing the breast 24 against the biopsy grid 54.

The concave lower portion 102 of the bladder 90 also presses upward against the anterior breast 24.

As shown in FIGS. 1 and 2, the biopsy grid 54 is positioned adjacent the lateral side of the breast 24 and the bladder 90 moves forward against the medial side of the breast 24 to compress the breast 24 against the biopsy grid 54. It is understood that the biopsy grid 54 may alternatively be positioned adjacent the medial side of the breast 24 and the bladder 90 moves rearward against the lateral side of the breast 24 to compress the breast 24 against the biopsy grid 54. Following expansion of the bladder 90, the breast 24 may be manually maneuvered and repositioned to provide even compression of the breast tissue against the biopsy grid 54.

The pump 110 and medical grade tubing 114 may be removed from the bladder 90 or shielded prior to MRI scanning in order to eliminate or minimize image distortion. Alternatively, the pump 110 and medical grade tubing 114 may be made solely of MRI compatible materials and therefore may be connected to the bladder 90 during MRI scanning without interfering with the scan image.

The bladder 90 provides compression of the breast 24 with multiple degrees of freedom. The force of the bladder 90 applied against the breast 24 is in multiple dimensions which can provide improved compression of the outer areas or margins of the breast 24. Desirably, all medial/lateral areas of interest of the breast tissue are fully flush against the biopsy grid 54, where flush is when the grid square of the biopsy grid 54 is filled with tissue and the tension of the tissue allows for insertion of a biopsy needle without tissue movement.

It is understood that the bladder 90 may also comprise of multiple separate balloons or bladders 90 that are independently filled or have separately fillable compartments which may selectively act upon the breast 24 to provide deformation and compression to the breast 24.

The compression device 58 may be part of an open loop system or a closed loop system. In an open loop system, the user may receive pressure information from pressure sensors detecting, for example, the pressure of the compression device 58 or bladder 90, or tension of the breast 24 tissue, to manually adjust the expansion of the compression device 58 or bladder 90. The user may also manually feel the breast tissue without sensors 116 in order to provide the desired expansion of the compression device 58 or bladder 90.

Figure 6:
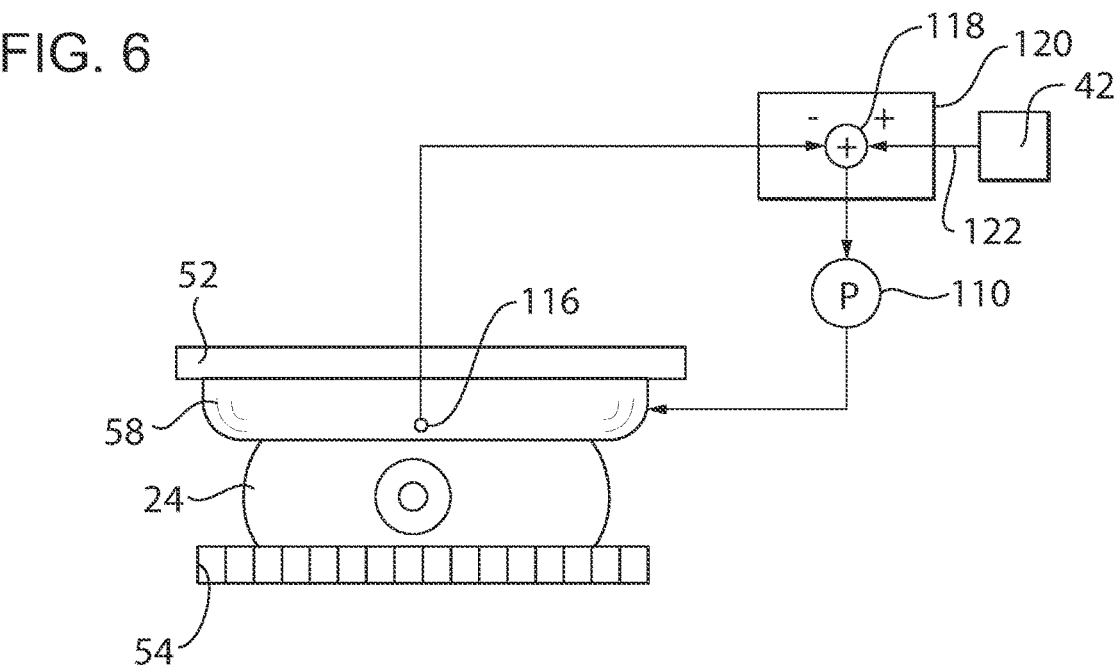
FIG. 6 is a schematic representation of a closed loop system operation of the compression device of FIG. 5.

Referring briefly to FIG. 6, in one embodiment of the present invention, the bladder 90 may be a part of a precise closed loop system which permits the pump 110 to communicate with a pressure sensor 116 detecting, for example, the pressure of the compression device 58 or bladder 90 or tension of the breast 24 tissue to provide control signal instructions to the pump 110 and to deliver the appropriate amount of compression and stabilization of the breast 24 by adjusting the amount of fluid filled into the bladder 90.

Sensing by the pressure sensor 116 may provide a displacement signal received at a summing junction 118 implemented through software in a memory executed by a processor of the control microcontroller 120. The summing junction 118 also receives a command signal 122, for example, provided by input from the user and describing a pressure, tension or displacement of the bladder 90 or the breast 24 tissue. An output from the summing junction 118 provides a signal to continue or cease inflation by the pump 110.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "an electronic computer" and "a processor" or "the microprocessor" and "the processor," can be understood to include one or more of these devices that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

References to "a processor" should be understood to include electronic computers, microprocessors, microcontrollers, FPGA devices, ASIC devices and similar programmable or program defined electronic circuits and collections of such devices that can communicate in a stand-alone and/or a distributed environment(s) and can thus be configured to communicate via wired or wireless communications with other processors. Furthermore, references to memory, unless otherwise specified, can include one or more processor-readable and accessible memory elements and/or components that can be internal to the processor or external to the processor and accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A breast immobilization device for magnetic resonance imaging (MRI) assisted biopsy of a breast having a medial or lateral side of the breast extending along a biopsy grid extending along a plane and an opposite side of the breast extending along a flat plate extending parallel to the plane, the device comprising:
    an expandable volume positioned between the biopsy grid and the flat plate, in a first unexpanded position, having a first thickness measured perpendicular to the plane, and in a second expanded position, having a second thickness measured perpendicular to the plane that is greater than the first thickness;
    wherein the volume in the second expanded position exerts a force against the opposite side of the breast to press the medial or lateral side of the breast against the biopsy grid.

2. The device of claim 1 wherein the expandable volume is an inflatable bladder comprising an elastomeric housing.

3. The device of claim 2 wherein the housing provides a planar attachment surface opposite a concave contact surface contacting a margin of the breast.

4. The device of claim 2 wherein the housing provides a J-shaped cross section taken perpendicular to the plane.

5. The device of claim 2 wherein the housing is fillable with a fluid.

6. The device of claim 5 wherein the fluid is at least one of air or normal saline.

7. The device of claim 2 further comprising a pump configured to fill the housing with a fluid.

8. The device of claim 7 wherein the pump is a manual balloon pump.

9. The device of claim 7 wherein the pump is an electric air compressor.

10. The device of claim 1 wherein the volume is a memory foam.

11. The device of claim 10 wherein the volume further comprises a plate pivotable with respect to the expandable volume to pivot toward the opposite side of the breast when the expandable volume goes from the first unexpanded position to the second expanded position.

12. The device of claim 11 wherein the memory foam is positionable between the pivotable plate and the flat plate.

13. The device of claim 1 further comprising the biopsy grid and flat plate wherein the expandable volume is attachable to the flat plate.

14. The device of claim 1 wherein a difference between the first thickness and the second thickness is at least 1.5 inches.

15. The device of claim 14 wherein a difference between the first thickness and the second thickness is at least 3 inches.

16. A method of breast immobilization for magnetic resonance imaging (MRI) assisted biopsy of a patient breast, the method comprising:

extending a medial or lateral side of the patient breast along a biopsy grid extending along a plane and an opposite side of the breast along a flat plate extending parallel to the plane;

positioning an expandable volume between the biopsy grid and the flat plate, wherein in a first unexpanded position, the volume has a first thickness measured perpendicular to the plane, and in a second expanded position, the volume has a second thickness measured perpendicular to the plane that is greater than the first thickness;

exerting a force against the opposite side of the breast to press the medial or lateral side of the breast against the biopsy grid in the second expanded position of the volume.

17. The method of claim 16 wherein the expandable volume is an inflatable bladder and the method further comprises filling the inflatable bladder with a fluid.

18. The method of claim 16 wherein the expandable volume is a memory foam and the method further comprises compressing the memory foam and then allowing the memory foam to return to its original state.

\* \* \* \* \*